(12) United States Patent
Magni

(10) Patent No.: US 7,396,386 B2
(45) Date of Patent: Jul. 8, 2008

(54) METHOD AND APPARATUS FOR KEEPING CONSTANT THE RETENTION TIMES IN A GASCHROMATOGRAPHIC ANALYSIS

(75) Inventor: Paolo Magni, Izano (IT)

(73) Assignee: Thermo Electron S.p.A., Rodano (IT)

( * ) Notice: Subject to any disclaimer, the term of this patent is extended or adjusted under 35 U.S.C. 154(b) by 161 days.

(21) Appl. No.: 10/537,768

(22) PCT Filed: Dec. 5, 2003

(86) PCT No.: PCT/IB03/05706

§ 371 (c)(1),
(2), (4) Date: Sep. 26, 2005

(87) PCT Pub. No.: WO2004/053478

PCT Pub. Date: Jun. 24, 2004

(65) Prior Publication Data
US 2006/0123987 A1    Jun. 15, 2006

(30) Foreign Application Priority Data
Dec. 9, 2002    (IT)    .............................. MI02A2605

(51) Int. Cl.
B01D 53/02    (2006.01)

(52) U.S. Cl. ........................... 95/82; 96/102; 73/23.36; 73/23.42

(58) Field of Classification Search .............. 95/82, 95/85, 87; 96/101, 102, 103, 105; 73/23.35, 73/23.36, 23.41, 23.42; 422/89

See application file for complete search history.

(56) References Cited

U.S. PATENT DOCUMENTS

| 4,994,096 | A | * | 2/1991 | Klein et al. .................... 95/15 |
| 5,545,252 | A | * | 8/1996 | Hinshaw et al. ................ 95/15 |
| 5,711,786 | A | * | 1/1998 | Hinshaw ........................ 95/82 |
| 5,859,360 | A | * | 1/1999 | Magni et al. ................ 73/19.05 |

(Continued)

FOREIGN PATENT DOCUMENTS

EP    0 840 116 A1    5/1998

(Continued)

OTHER PUBLICATIONS

International Search Report of PCT/IB03/05706 mailed Apr. 23, 2004.

(Continued)

Primary Examiner—Duane Smith
Assistant Examiner—Robert A Clemente
(74) Attorney, Agent, or Firm—Nixon & Vanderhye P.C.

(57) ABSTRACT

A method for obtaining reproducibility of the retention times of the components of a mixture to be analysed in an apparatus for gaschromatographic analysis provided with a capillary column, when there occurs one of the following variations: variation in the length of the column, or alternatively its replacement with a column having identical real specifications with the exception of the length, and/or variation in the pressure of the carrier gas at output from said column. The method envisages that the pneumatic resistance of the column is known and preferably measured before and after the aforesaid variations, and that a new input pressure or a new mass flow of the carrier gas will be entered into said apparatus for gaschromatographic analysis in relation to said values of pneumatic resistance.

7 Claims, 5 Drawing Sheets

U.S. PATENT DOCUMENTS

| | | | |
|---|---|---|---|
| 5,915,269 A * | 6/1999 | Cahill et al. | 73/23.35 |
| 5,958,246 A * | 9/1999 | Tipler et al. | 210/656 |
| 5,987,959 A * | 11/1999 | Klee et al. | 73/1.02 |
| 6,036,747 A | 3/2000 | Blumberg et al. | |
| 6,165,251 A * | 12/2000 | Lemieux et al. | 95/82 |
| 6,357,277 B1 * | 3/2002 | Pigozzo et al. | 73/23.22 |
| 6,494,078 B1 * | 12/2002 | Klee | 73/23.35 |
| 7,135,056 B2 * | 11/2006 | Henderson | 95/82 |
| 2005/0178266 A1 * | 8/2005 | Henderson | 95/82 |

FOREIGN PATENT DOCUMENTS

| | | |
|---|---|---|
| EP | 0 872 732 A1 | 10/1998 |
| EP | 1 041 382 A2 | 10/2000 |

OTHER PUBLICATIONS

L.M. Blumberg et al., "Method Translation and Retention Time Locking in Partition GC", Analytical Chemistry, vol. 70, No. 18, Sep. 15, 1998, pp. 3828-3839, XP002276489.

* cited by examiner

US 7,396,386 B2

METHOD AND APPARATUS FOR KEEPING CONSTANT THE RETENTION TIMES IN A GASCHROMATOGRAPHIC ANALYSIS

This application is the US national phase of international application PCT/IB2003/005706 filed 5 Dec. 2003, which designated the U.S. and claims priority of IT MI2002A 002605, filed 9 Dec. 2002, the entire contents of each of which are hereby incorporated by reference.

TECHNICAL FIELD

The present invention relates to a method for maintaining the retention times of the components of a mixture to be analysed constant in an apparatus for gaschromatographic analysis provided with a capillary column, when there is a variation in the length of said capillary column and/or a variation in the output pressure from said column.

PRIOR ART

For the analysis of a specimen of a given mixture in a gaschromatographic apparatus, a known practice is to use a capillary column, having predefined stationary phase and nominal dimensions, in which the mixture to be analysed is made to pass in the gaseous state, by means of an inert carrier gas (carrier), at an appropriate temperature, or temperature profile in time, at which the column itself is kept.

During passage of the gaseous mixture in the apparatus, the various components (or substances) have different times for traversing the capillary column as their own constituent parts vary, and hence the various substances reach a detector, set downstream of the column, in different times. There is thus obtained a separation in time of the components of the mixture which enables evaluation of the presence of each individual substance present. The said traversing times are referred to as retention times of the substances.

Consequently, downstream of the capillary column, there arrive, at different instants, different amounts of homogeneous substances, and the detector is able to measure the amounts of these substances, producing a graphic representation, referred to as chromatogram, which shows a series of consecutive peaks. The peaks are plotted on a cartesian graph, on the ordinate of which is a scale of measurements proportional to the amount of the substance and on the abscissa of which is the time elapsing from introduction of the specimen into the apparatus.

Given a type of column and the operating conditions, the retention time is characteristic for each substance and constitutes the parameter used for identification of the individual substance (component) that is detected.

In everyday use of gaschromatographic apparatus, it is common practice to cut the capillary column for the purpose of excluding terminal portions thereof that could be degraded after numerous analyses. This degradation can derive from possible non-vaporized by-products present in the specimen that accumulate in the initial portion of the column and/or from the possible overheating of the terminal portion of the column inside the detector.

It is likewise common practice to change the type of detector downstream of the capillary column according to the particular requirements of the analysis. The different detectors that may be used can operate at different pressures, and in particular it is common practice to use detectors that operate at atmospheric pressure and detectors that operate in the presence of a vacuum (mass spectrometer).

The above modifications, which do not necessarily envisage any replacement of the column and which are particularly frequent during the use of the apparatus, lead to a variation in the conditions of analysis and cause a modification of the retention times for the different substances that make up one and the same mixture.

In other words, the analysis of one and the same mixture of substances before and after the aforesaid modifications, i.e., before and after cutting of the capillary column and/or the variation in the output pressure from the column, involves, all the other conditions being equal, the variation in the retention times, this resulting in the detriment of the identification of the components of the mixture under examination. The variation in the retention times thus imposes a recalibration of the apparatus and/or a modification of the parameters of analysis in order to render comparable the results obtained before and after said modifications, these being activities which involve, in common practice, a considerable expenditure in terms of time and resources.

There is consequently a widespread requirement of having available a method and an apparatus which, by detecting small amounts indicating the state of the system, will be able to determine new functional parameters that will lead, after variation in length of the column and/or in the output pressure, to obtaining chromatograms that are immediately comparable with one another, i.e., that will enable the retention times to be maintained constant for each component analysed.

For the above purpose, there is known a method, proposed in the U.S. Pat. No. 6,036,747, which envisages, after detection of some state parameters prior to variation in the apparatus and setting of the new values of length of the column or output pressure, obtaining a value of the input pressure of the carrier gas to be imposed on the system after said variations. This new value of the input pressure is calculated on the basis of three different formulae in relation to the initial value that the output pressure assumes. The method proposed is, however, somewhat complex to implement and, given the multiplicity of relations for calculation of the new value, does not always lead to reliable values. The method moreover requires the knowledge of the geometrical parameters of the column (length and internal diameter), which are far from easy to measure with accuracy.

The patent EP-B-0.741.867, in the name of the present applicant, teaches how to measure experimentally, by means of a test with just the carrier, a constant K that is a function of the geometrical parameters of the column used in the apparatus for gaschromatographic analysis, for the purpose of providing a simple and reliable method for controlling the flow rate in the gaschromatographic apparatus itself. This patent right does not, however, contain any indications regarding the use of said constant K, defined also as the inverse of the pneumatic resistance of the column, in order to maintain the retention times constant as the geometrical parameters of the column vary or as the output pressure from the latter varies, said pressure being determined by the detector used for the analysis.

A purpose of the present invention is to provide a method and an apparatus which, as the length of the column varies and/or the output pressure varies, enables the same retention times of the substances of a mixture to be obtained before and after said variation, in the case where the temperatures of the column are maintained; the same, instant by instant, starting from when the specimen is introduced into the apparatus.

Another purpose of the present invention is to provide a method and an apparatus that will enable, starting from simple measurements of the state of the system, precise values of pressure and/or of flow rate of the carrier gas to be obtained, which are to be set after a variation in length of the column and/or in the output pressure of the carrier gas, for the purpose of obtaining the aforesaid same retention times for the same substances, before and after said variations.

SUMMARY OF THE INVENTION

According to the present invention, the method for obtaining the reproducibility of the retention times of the components of a mixture to be analysed in an apparatus for gaschromatographic analysis provided with a capillary column when one of the following variations occurs: namely variation in the length of the column, or alternatively replacement of the column with a column having identical real specifications with the exception of the length, and/or variation in the pressure of the carrier gas at output from said column—envisages that the temperature or temperature profile will be maintained unvaried, instant by instant, starting from the introduction of the mixture to be analysed into the apparatus, for each analysis of the mixture. The method moreover envisages that the pneumatic resistance of the column $KC_{old}=K(L_{old})$ is known prior to the aforesaid variations, the analytical expression of which is $$K(L_{old}) = \frac{256 \cdot L_{old}}{\pi \cdot d^4} \cdot \frac{\eta_0 \cdot P_{ref}}{T_{ref}^{1+\alpha}} \quad (9)$$

where:
- d is the diameter of the column;
- $P_{ref}$, $T_{ref}$ are, respectively, the reference pressure and the reference temperature (referred to the standard conditions);
- $\eta_0$ is the viscosity of the carrier gas under the reference conditions;
- $L_{old}$ is the initial length of the column; and
- $\alpha$ is the coefficient depending upon the type of carrier gas used;

and further envisages that, prior to the variations in the length of the column and/or in the output pressure, the pressure $p_{i,old}$ of the carrier gas will be detected at a point corresponding to the input section of the column, and the pressure $p_{o,old}$ of the carrier gas will be detected at a point corresponding to the output section of the column. Furthermore, after the aforesaid variations, the method envisages that the new pneumatic resistance of the column $KC_{new}=K(L_{new})$ will be detected, the analytical expression of which is $$K(L_{new}) = \frac{256 \cdot L_{new}}{\pi \cdot d^4} \cdot \frac{\eta_0 \cdot P_{ref}}{T_{ref}^{1+\alpha}} \quad (5)$$

where:
- $L_{new}$ is the new length of the column;

and further envisages that the possible new pressure $p_{o,new}$ at output from the column will be selected.

Then the method according to the invention envisages calculation of a new input pressure $p_{i,new}$ or of a new mass flow $F_{new}$ (referred to standard conditions) of the carrier gas, using the following relation:

$$\lambda = \frac{j_{old}}{j_{new}} \cdot g \cdot \frac{p_{o,new}}{p_{o,old}}$$

where:

$$g = \frac{K(L_{new})}{K(L_{old})} = \frac{L_{new}}{L_{old}}$$

$$j_{new} = \frac{3}{2} \cdot \frac{\left(\frac{p_{i,new}}{p_{o,new}}\right)^2 - 1}{\left(\frac{p_{i,new}}{p_{o,new}}\right)^3 - 1}$$

$$j_{old} = \frac{3}{2} \cdot \frac{\left(\frac{p_{i,old}}{p_{o,old}}\right)^2 - 1}{\left(\frac{p_{i,old}}{p_{o,old}}\right)^3 - 1}$$

and the setting of the new input pressure $p_{i,new}$ or of the new mass flow $F_{new}$ of the carrier gas into said apparatus for gaschromatographic analysis in correlation to $\lambda$.

It may be noted that the pneumatic resistance KC ($KC_{old}$ or $KC_{new}$) defined analytically above, and to which reference will be made in what follows, is for convenience of calculation the inverse of the constant K defined in the above-mentioned patent EP-B-0.741.867, filed in the name of the present applicant.

BRIEF DESCRIPTION OF THE DRAWINGS

Described in what follows are some particular embodiments of the method according to the present invention and of an apparatus designed to implement one or more of said method, said embodiments being provided purely by way of non-limiting example, with the aid of the attached figures, in which.

DETAILED DESCRIPTION OF SOME EMBODIMENTS OF THE INVENTION

Figure 1:
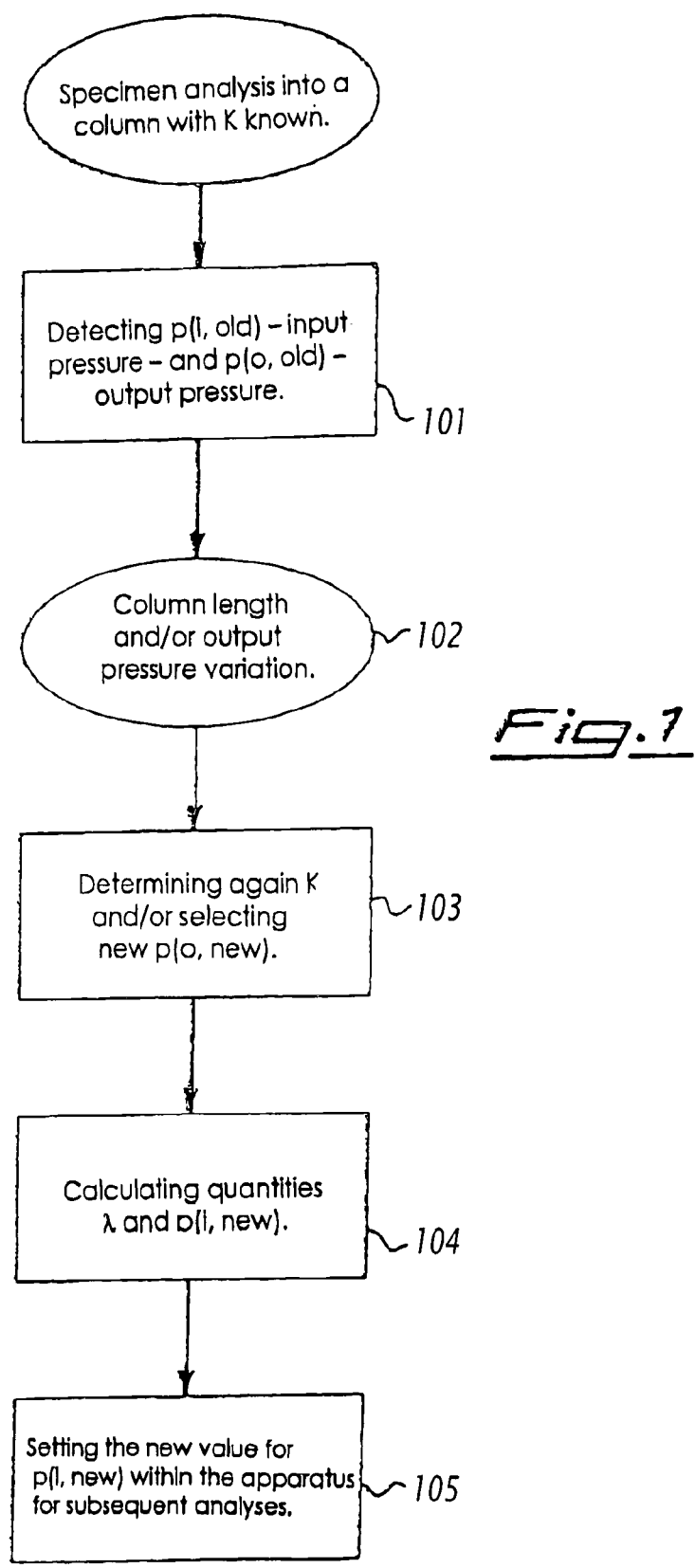
FIG. 1 is a block diagram of a particular embodiment of the method according to the present invention.

During gaschromatographic analysis of a given mixture in an apparatus provided with a capillary column, for any one component of said mixture, the retention time in a given column j can be defined as $$t_{r,j} = t_{0,j} \cdot (1 + k_j)$$

where:
$t_{0,j}$ is the so-called "dead" time, defined by the following relation:

$$t_{0,j} = \frac{L_j}{\bar{u}_j}$$

$k_j$ is a ratio of capacity (defined as "capacity factor");
$L_j$ is the length of the column j; and
$\bar{u}_j$ is the mean linear velocity of the carrier gas in the column j.

Considering now two capillary columns, one designated by the subscript "old" and the other by the subscript "new", which have the some internal diameter and the same stationary-phase thickness, it is possible to show that $$\frac{t_{r,old}}{t_{r,new}} = \frac{t_{0,old}}{t_{0,new}}$$

whence it is found that the retention times of the same component in two columns which have only their lengths different are the same if the times $t_0$ in the two columns are the same.

However, the dead time $t_0$ in a given column of length L is defined, as already given above, as $$t_0 = \frac{L}{\bar{u}}$$

where $\bar{u}$ is the mean linear velocity of the carrier gas (carrier) in the column; and
L is the length of the column.

Now, introducing the pneumatic resistance of a column, which can advantageously be calculated empirically, as emerges from the European patent EP-B-0.741.867, filed in the name of the present applicant, and which has the analytical expression $$KC = \frac{256 \cdot L}{\pi \cdot d^4} \cdot \frac{\eta_{std} \cdot p_{std}}{T_{std}^{1+\alpha}} \quad \text{(i)}$$

where:
d is the diameter of the column;
$p_{std}$ and $T_{std}$ are the reference pressure and the reference temperature, respectively (under standard conditions);
$\eta_{std}$ is the viscosity of the carrier gas under reference conditions;
L is the length of the column;
$\alpha$ is the coefficient of dependence of the viscosity upon the temperature, which is a function of the particular type of carrier gas used (where $0<\alpha<1$);

it is found that, given the same diameter of the two columns ("old" and "new") which have only their lengths different, the following relation applies:

$$\frac{L_{new}}{L_{old}} = \frac{KC_{new}}{KC_{old}}$$

and consequently, by imposing $t_{0,1}=t_{0,2}$, we have $$\frac{L_{old}}{\bar{u}_{old}} = \frac{L_{new}}{\bar{u}_{new}} \quad \text{(ii)}$$

$$\bar{u}_{new} = \bar{u}_{old} \cdot \frac{KC_{new}}{KC_{old}}$$

The above relation indicates that, in order to maintain the retention times of a given substance constant as the length of a column varies, but given the same diameter of the column and thickness of the stationary phase of the latter, it is sufficient to enter a new mean velocity of the carrier gas that is directly proportional—but for a constant that depends upon said variation in length—to the mean velocity of the carrier gas before the variation.

However, in a normal apparatus for gaschromatographic analysis it is not possible to set this mean velocity directly (unless the actual values of length and diameter of the column are accurately known), whilst it is common practice to enter the pressure $p_i$ of the carrier gas at input to the column, or else the mass flow F of said gas.

Introducing now the corrective factor of the pressure gradient, defined as $$j = \frac{3}{2} \cdot \frac{(p_i/p_o)^2 - 1}{(p_i/p_o)^3 - 1} \quad \text{(iii)}$$

where $p_i$ is the pressure of the carrier gas at input to the column; and $p_o$ is the pressure of the carrier gas at output from the column, the mean velocity of the carrier gas con be expressed as a function of the velocity of output of the gas from the column $u_o$, as $$\bar{u} = j \cdot u_o \quad \text{(iv)}$$

But, the output velocity $u_o$ can be expressed as a function of the flow rate (measured under the effective thermodynamic conditions of the apparatus) in the column as $$u_o = \frac{4}{\pi \cdot d^2} \cdot F_o^{T_{col}} \quad \text{(v)}$$

where d is the diameter of the column; and
$T_{col}$ is the temperature of the column, and referring the flow rate to standard conditions (101 kPa, 20° C.) via the following relation:

$$F = F_o^{T_{col}} \cdot \frac{T_{std}}{T_{col}} \cdot \frac{p_p}{p_{std}} \quad \text{(vi)}$$

where $T_{std}$ and $p_{std}$ are, respectively, the standard temperature and standard pressure; and $p_o$ is the output pressure from the column, we have $$u_o = F \cdot \frac{T_{col}}{T_{std}} \cdot \frac{p_{std}}{p_{col}} \cdot \frac{4}{\pi \cdot d^2} \quad \text{(vii)}$$

Consequently, introducing now the subscripts "old" and "new" to designate, respectively, the column of initial length and the column of modified length, recalling that the real diameter is the same and assuming that the output pressure may vary, it is found (considering the ratio between velocity of the carrier gas at output from the column) that $$\frac{u_{o,new}}{u_{o,old}} = \frac{F_{new}}{F_{old}} \cdot \frac{p_{o,old}}{p_{o,new}} \quad \text{(viii)}$$

and considering now relation (ii), which imposes the constancy of the retention times, and the subsequent equation (iv), we have $$\frac{u_{o,new}}{u_{o,old}} = \frac{F_{new}}{F_{old}} \cdot \frac{p_{o,old}}{p_{o,new}} = \frac{j_{old}}{j_{new}} \cdot \frac{KC_{new}}{KC_{old}} \quad \text{(ix)}$$

where $$j_{new} = \frac{3}{2} \cdot \frac{\left(\frac{p_{i,new}}{p_{o,new}}\right)^2 - 1}{\left(\frac{p_{i,new}}{p_{o,new}}\right)^3 - 1}$$

$$j_{old} = \frac{3}{2} \cdot \frac{\left(\frac{p_{i,old}}{p_{o,old}}\right)^2 - 1}{\left(\frac{p_{i,old}}{p_{o,old}}\right)^3 - 1}$$

i.e., designating as $\lambda$ the following quantity:

$$\lambda = \frac{j_{old}}{j_{new}} \cdot g \cdot \frac{p_{o,new}}{p_{o,old}} \quad \text{(x)}$$

where $$g = \frac{KC_{new}}{KC_{old}} = \frac{L_{new}}{L_{old}} \quad \text{(xi)}$$

we obtain the following relation:

$$F_{new} = F_{old} \cdot \lambda \quad \text{(xii)}$$

This relation indicates that, to obtain the same retention times for one and the same substance, when the length of the capillary column is modified and/or the output pressure of the carrier gas is modified, it is necessary to enter a new mass flow $F_{new}$ of the carrier gas proportional, via the parameter $\lambda$, to the mass flow $F_{old}$ recorded, or calculated, prior to the aforesaid modifications.

It may be noted that relation (xii) is valid only in the case where the analyses performed before and after the variation in length of the column and/or the variation in output pressure are performed, maintaining the actual diameter of the column and the temperature ($T_{col}$) of the column constant instant by instant (starting from introduction of the mixture to be analysed).

Furthermore, as may be appreciated from the foregoing equations, the mass flow F depends strictly upon the temperature that the column assumes and consequently, in the case where for the analysis of a given specimen it were necessary to enter a program of temperatures in time, it would become necessary to calculate and control the new mass flow $F_{new}$, instant by instant.

Since frequently during an analysis the temperature follows a predefined temporal trend (and hence is a function of time), if the aim is to operate with a constant flow of the carrier gas, it will be necessary to detect, as the temperature varies, the quantity $p_i$ and then calculate the quantity j. This requisite renders it more difficult to maintain the flow of the carrier gas under control, according to relation (xii), in order to maintain the retention times constant.

It is, on the other hand, possible to express the flow rate F as a function of the pressures of the carrier gas at input to and output from the column, as follows:

$$F = \frac{p_i^2 - p_o^2}{KC \cdot T_{col}^{1+\alpha}} \quad \text{(xiii)}$$

and recalling that the program of the temperature $T_{col}$ and the real diameter of the column are the same both before and after the variations in length of the column and/or in output pressure, we can write $$\frac{p_{i,new}^2 - p_{o,new}^2}{p_{i,old}^2 - p_{o,old}^2} = \lambda \cdot g$$

i.e., we obtain $$p_{i,new} = \sqrt{p_{o,new}^2 + \lambda \cdot g \cdot (p_{i,old}^2 - p_{o,old}^2)} \quad \text{(xiv)}.$$

It may be noted that this relation does not depend upon the mass flow F and is consequently independent of the particular temperature profile followed in time for carrying out the analysis. That is, relation (xiv) does not presuppose calculation instant by instant of the input pressure of the carrier gas to be set in the apparatus after the variation in length of the column and/or in the output pressure.

Consequently, to obtain the same retention times of a substance as the length of the column varies and/or the output pressure of the carrier gas varies, under the hypothesis that the actual diameter of the column, the thickness of the stationary phase, and the temperature program are kept constant, it is sufficient to enter the new input pressure of the carrier gas, according to what is defined by relation (xiv).

Said relation (xiv), as likewise relation (xii), is not linear, i.e., since the quantity $j_{new}$ depends upon $p_{i,new}$ and hence upon $F_{new}$, for the analytical solution of the two equations it is necessary to use a method of successive approximations. However, it may readily be shown that this method converges in a few passages towards an optimal solution. From the relations given above, it is evident for a person skilled in the branch that, given the inaccuracy (and sometimes the impossibility on account of the small dimensions of the capillary columns) of a direct measurement of the real geometrical characteristics of the column (length and diameter) before and/or after the variations in length of the column and/or in output pressure, it is extremely advantageous to be able to detect the pneumatic resistance of the column KC, which, since it may be derived empirically (see the patent EP-B-0.741.867) by means of a blank test of the apparatus, i.e., with just the carrier, enables precise calculation of the ratio g (equation (xi)) and of the parameter $\lambda$ (equation (x)).

In particular, the value of KC of equation (i) can be determined, as may be deduced from relation (xiii) by measuring, during a blank test, the input flow $F_{st}$ referred to the standard conditions, the temperature $T_{col}$ of the column, and the input and output pressures, $p_i$ and $p_o$ respectively, of the column, according to the following relation:

$$KC = \frac{p_i^2 - p_o^2}{F_{st} \cdot T_{col}^{1+\alpha}}. \quad \text{(xiii.bis)}$$

From what has been discussed above, it is found that in the case where, in laboratory practice, it becomes necessary to cut the column or vary the type of detector set downstream of the column itself, and hence vary the output pressure, it is sufficient to measure—prior to the variation—the quantities:

$KC_{old}$, which is the pneumatic resistance of the column (possibly measured by means of a blank test), and the analytical expression of which is, analogously to equation (i), as given below:

$$KC_{old} = K(L_{old}) = \frac{256 \cdot L_{old}}{\pi \cdot d^4} \cdot \frac{\eta_0 \cdot P_{ref}}{T_{ref}^{1+\alpha}} \quad \text{(i.bis)}$$

wherein:
$L_{old}$ is the length of the column before a variation thereof;
$p_{i,old}$, which is the input pressure of the carrier gas (measurable);
$p_{o,old}$, which is the output pressure of the carrier gas (known);
possibly (if we proceed using equation (xii)) $F_{old}$ or $T_{col}$, which are the mass flow in standard conditions and the effective temperature of the column, respectively;

and, following upon the variations, the quantities:
$p_{o,new}$, which is the expected output pressure (known); and
$KC_{new}$, which is the new pneumatic resistance of the column (measured for example according to what is described in EP-B-0.741.867) and the analytical expression of which is:

$$KC_{new} = K(L_{new}) = \frac{256 \cdot L_{new}}{\pi \cdot d^4} \cdot \frac{\eta_0 \cdot P_{ref}}{T_{ref}^{1+\alpha}} \quad \text{(i.ter)};$$

where $L_{new}$ is the length of the column after its (possible) variation, in order to obtain from relations (xiv) or (xii) the new values $p_{i,new}$ (input pressure) or $F_{new}$ (flow rate under standard conditions) with which to set the apparatus to obtain the constancy of the retention times.

Figure 3:
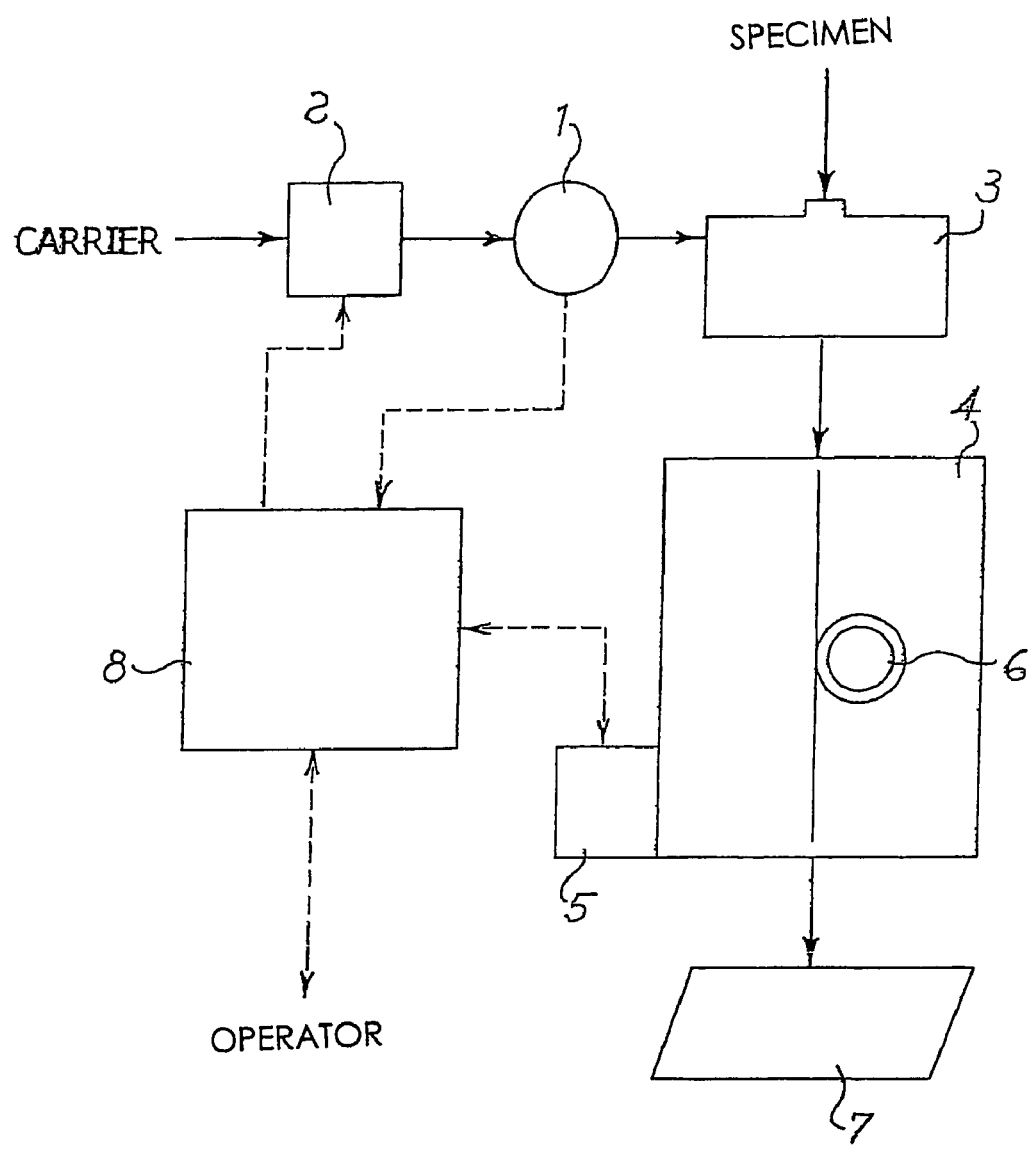
FIG. 3 is a diagram of an apparatus designed to implement the method represented in FIG. 1.

With reference to FIG. 1, described herein is a method for maintaining the retention times constant for the analysis of a mixture after the variation in length of the capillary column and/or the variation in the output pressure of the carrier gas, where the length of the column is not known, but its initial pneumatic resistance $KC_{old}$ (for example, measured via an experimental blank test) is known, and in which there is available an apparatus, such as the one represented schematically in FIG. 3, which enables maintaining the input pressure $p_i$ of the carrier gas constant.

The method envisages (step 101) recording, prior to the aforesaid variation or variations, the pressure of the carrier gas at input $p_{i,old}$ and the pressure of the gas at output $p_{o,old}$, the latter depending upon the type of device for analysis that is set downstream of the capillary column.

After the variations in the length of the column and/or in the output pressure (step 102), it is necessary to determine again (step 103) the constant of resistance of the column $KC_{new}$. Said value $KC_{new}$ can be determined automatically by the apparatus for analysis, by means of, for example, a so-called blank test, i.e., by causing only carrier gas to flow, in stabilized conditions of flow rate, and subsequently measuring or setting the values $T_{col}$, $p_i$, F (and possibly $p_o$ if this is not known), according to relation (xiii).

Once the value of $KC_{new}$ is thus known, which depends, under the hypotheses made, uniquely upon the new length assumed by the column (see relation (i)), it is possible to set conveniently (step 104), using equation (x), the analytical expression given by relation (xiv) and then solve the latter by means of successive approximations.

The value of $p_{i,new}$ thus calculated must now be set (step 105) into the apparatus for analysis as new input pressure of the carrier gas in order to maintain the retention times of the various components of the mixture to be analysed constant before and after the aforesaid variations in length of the column and/or in output pressure of the carrier gas.

In the event of the variation undergone by the apparatus consisting only of the variation in output pressure, it would not be necessary to re-determine the constant KC of the column (which remains unvaried), and thus step 103 should not be executed.

As already mentioned, the method described can be implemented using the apparatus for gaschromatographic analysis represented schematically in FIG. 3, in which there are present, on the line for introduction of the carrier gas, a device 1 for detection of the input pressure of the carrier, and means 2 for regulating said pressure, as well as an injection system 3 for input of the mixture to be analysed, which at output directs the flow of gas towards a capillary column 6.

The apparatus moreover comprises an oven 4, the temperature of which is regulated by a control device 5, and a capillary column 6 of length L or pneumatic resistance KC known, housed within the oven 4 itself. Downstream of the column 6, there is moreover present a detector 7 for the gases at output from the column, which is designed to measure the amount of the gases that flow from the column 6 itself.

The apparatus moreover comprises storage and processing means 8 (usually an electronic processor), which interface both with the operator and with the device for detection of the pressure 1, and govern the control device 5 and the means 2 for regulation of the input pressure of the carrier. During normal operation, the constant of resistance $KC_{old}$ of the column 6, is stored in these means 8, and the input pressure of the carrier gas $p_{i,new}$ is measured and stored. Consequently, as the length of the column 6 and/or the output pressure of the carrier gas vary/varies following upon the replacement of the detector 7, the operator sets, and starts execution of, an appropriate control program, possibly already present in the electronic processor 8, which has the job of determining, for example via a blank test as described in EP-B-0.741.867, the new value of the constant $KC_{new}$ and of prompting the operator for the possible new value of the output pressure $p_{o,new}$.

Then, the electronic processor 8 calculates, via successive approximations, the new value $p_{i,new}$ that the input pressure of the carrier must assume so that the retention times will remain constant for each substance, and, when a new analysis is performed, sets said new pressure $p_{i,new}$ by acting on the means 2 for regulating the pressure of the carrier at input.

Figure 2:
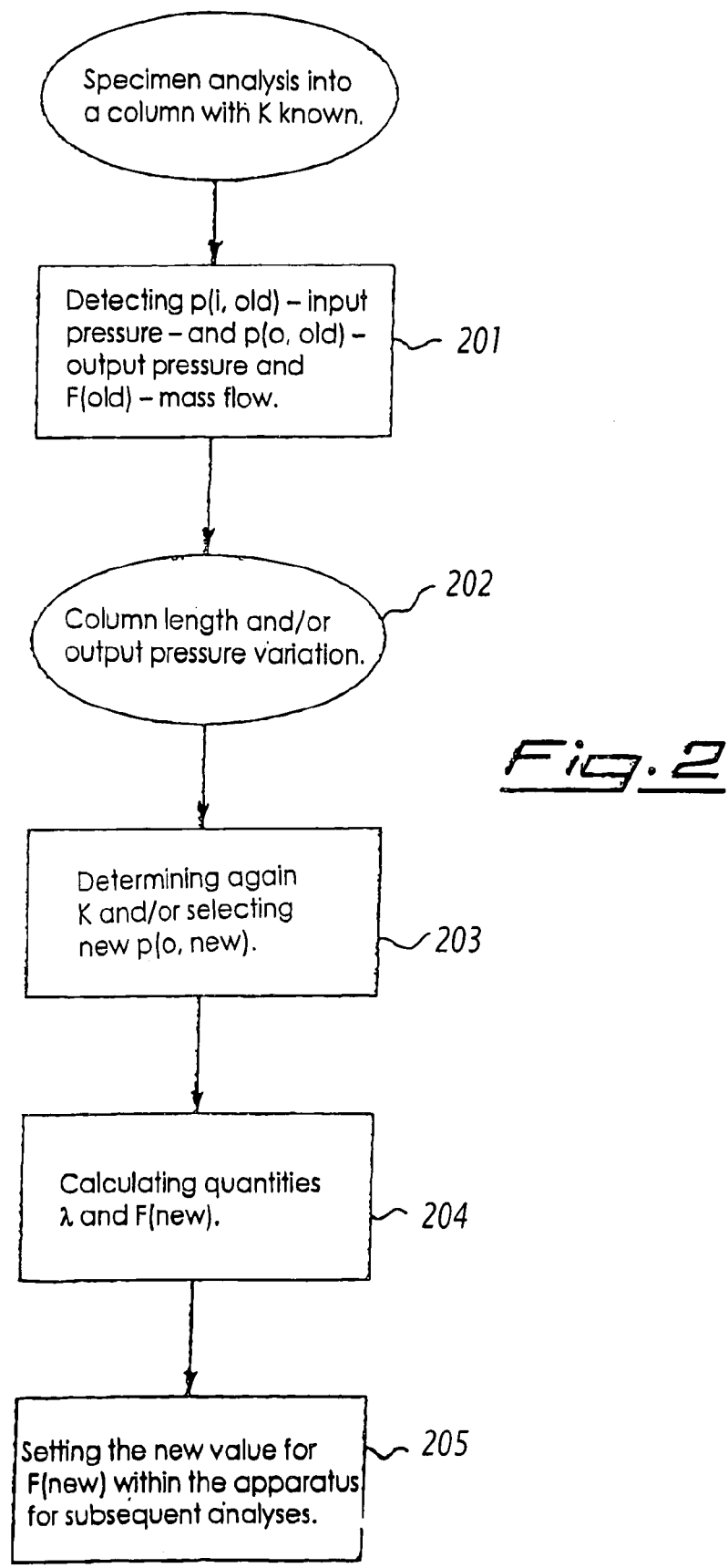
FIG. 2 is a block diagram of another embodiment of the method according to the present invention.

Alternatively, or in addition, the apparatus may comprise means for measuring the mass flow F of the carrier gas, possibly referred to standard conditions, and means for regulating this flow (not illustrated). There may likewise be provided a detector for detection of the output pressure of the carrier gas (not illustrated). FIG. 2 illustrates, instead, a method for maintaining the retention times constant after variation in the length of the column and/or in the output pressure of the carrier, whereby it is envisaged to control the mass flow of the carrier and whereby the value $KC_{old}$ of the constant of resistance of the column is known.

In a way similar to the method illustrated in FIG. 1, there is envisaged a step 201 in which, prior to the variations of the apparatus, there is carried out the measurement of the input pressure $p_{i,old}$ of the carrier, of the output pressure $p_{o,old}$ (if it is not known already) and, unlike the method illustrated in FIG. 1, of the mass flow $F_{old}$, referred to standard conditions. The latter detection, as may readily be understood from the analysis of relation (xiii), can alternatively be replaced by measuring the temperature $T_{col}$ of the column in order to calculate the quantity $F_{old}$ itself. If the operation is carried out at constant flow, as the temperature $T_{col}$ varies also the input pressure $p_i$ will vary, which hence is to be calculated instant by instant.

After variation in length of the column and/or in the output pressure of the carrier (step 202), the subsequent step 203 envisages redetermining the constant $KC_{new}$ only if the variation in length of the column has occurred, and step 204 envisages calculating the new mass flow $F_{new}$ (equation (xii)) under standard conditions, whereby constancy of the retention times is to be obtained.

Finally, step 205 envisages this value $F_{new}$ being set into the apparatus for subsequent analyses.

The method represented schematically in FIG. 2, on account of its dependence upon the temperature variation during time, which renders it substantially suitable only for analysis at constant temperature, is rarely used.

Consequently, provided in what follows are two examples in which the retention times for a mixture to be analysed are kept constant, as the length of the column varies and the output pressure varies respectively, operating with constant input pressure of the carrier.

EXAMPLE 1

Figure 4A:
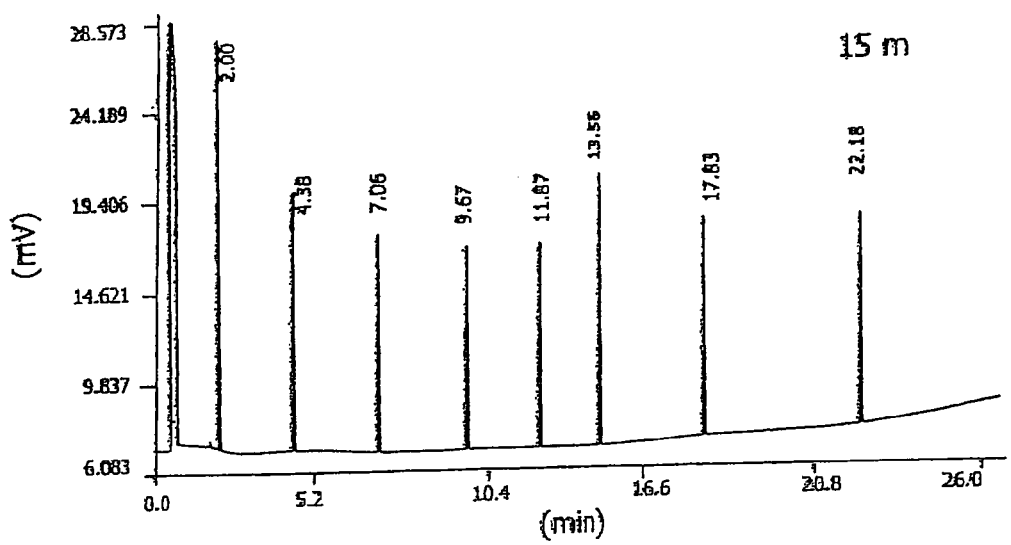
FIGS. 4a and 4b are, respectively, a chromatogram regarding the analysis of a given specimen with a capillary column 15 metres long and a chromatogram regarding the analysis, under the same temperature conditions, of the same specimen with the same capillary column shortened to approximately 13 metres.

A mixture underwent analysis to identify the amounts of compounds from C10 to C30 (i.e., mixtures of linear hydrocarbons with a number of carbon atoms ranging from 10 to 30) in a gaschromatographic apparatus provided originally with a capillary column of the 15 m×0.25 mm×0.25 μm DB5 type. The carrier gas was helium (He) maintained at a constant input pressure (relative pressure: 80 kPa), the temperature of the column followed a program that passed from 70° C. to 300° C. at a rate of 10° C./min, and the pneumatic resistance of the column was $KC_{old}$=0.6484. The output pressure was equal to the atmospheric pressure (101 kPa), and the results of the analysis are represented in the chromatogram provided in FIG. 4a (the ordinate represents an amount correlated to the amount of gas as it passes the detector downstream of the column, and the abscissa the time elapsed). Each of the peaks, which follow one another at determined time intervals, represents the measured amount of a certain component (see Table 1).

The column was then cut, by a length of approximately 2 metres, and the measurement of the pneumatic resistance was repeated, via a blank test (i.e., only with the carrier) according, for example, to the teachings of EP-B-0.741.867, and the result was $KC_{new}$=0.5649. The output pressure was not modified.

Calculation of the new input pressure (according to equation (xii)) led to defining the value $p_{i,new}$=60 kPa (relative pressure) as a new value of the input pressure of the carrier.

Figure 4B:
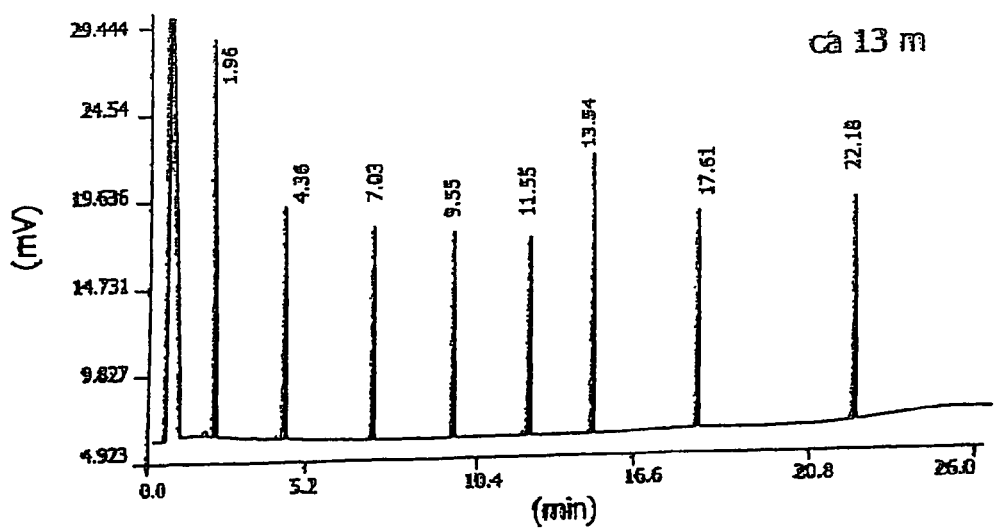

The same mixture was then analysed after variation of the length of the column, setting the new value of $p_{i,new}$ and maintaining the temperature program constant. The results of the analysis are given in the chromatogram in FIG. 4b.

A numeric representation of the retention times in the two cases is provided in Table 1.

TABLE 1

| Component | Retention times (original column) (min) | Retention times (cut column) (min) | Difference (absolute value) (min) |
|---|---|---|---|
| C10 | 2.00 | 1.98 | 0.02 |
| C12 | 4.38 | 4.35 | 0.03 |
| C14 | 7.05 | 7.03 | 0.02 |
| C16 | 9.57 | 9.55 | 0.02 |
| C18 | 11.87 | 11.85 | 0.02 |
| C20 | 13.96 | 13.94 | 0.02 |
| C24 | 17.63 | 17.61 | 0.02 |
| C30 | 22.19 | 22.19 | 0.00 |

EXAMPLE 2

Figure 5A:
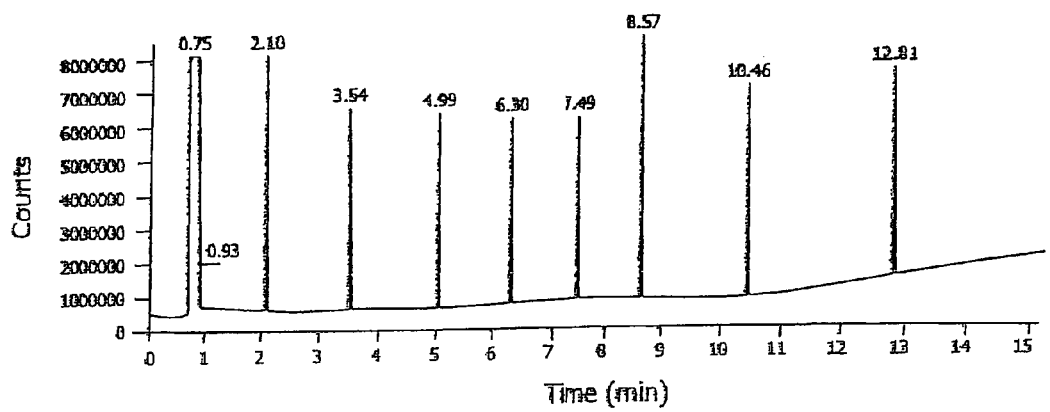
FIGS. 5a and 5b are, respectively, a chromatogram regarding the analysis of a given specimen with the use of a detector operating at atmospheric pressure (approximately 101 kPa) and a chromatogram regarding the analysis, under the same temperature conditions, of the same specimen with a detector operating in vacuum conditions (approximately $10^{-5}$ kPa).

A mixture underwent analysis to identify the amount of compounds from C10 to C30 (i.e., of linear hydrocarbons with a number of carbon atoms ranging between 10 and 30) in a gaschromatographic apparatus having a capillary column of the 30 m×0.32 mm×0.25 μm DB5 type, using a flame-ionisation detector (FID), operating at atmospheric pressure (101 kPa). The carrier gas was helium (He) maintained at a constant input pressure (relative pressure: 135 kPa), the temperature of the column followed a program that passed from 80° C. to 320° C. at a rate of 20° C./min, and the constant of resistance of the column was $KC_{old}$=0.6459. The results of the analysis are represented in the chromatogram provided in FIG. 5a, and the numeric evaluation of the retention times is given in Table 2.

The FID was then replaced by a mass spectrometer (MS), operating under vacuum conditions ($p_{o,new}$=$10^{-5}$ kPa), and the column remained unaltered (i.e., the pneumatic resistance of the column was not modified $KC_{old}$=$KC_{new}$).

Calculation of the new input pressure (according to equation (xii)), on the basis of the new output pressure $p_{o,new}$, led to the new value $p_{i,new}$=70 kPa (relative pressure) of the input pressure of the carrier. Note that not necessarily, when a mass spectrometer (operating under vacuum conditions, at approximately $10^{-5}$ kPa) is used, must the output pressure be known with precision, in so far as for values smaller than 1 kPa its absolute value no longer substantially affects the result of the calculation. For the purposes of calculation, the output pressure, when it approaches vacuum conditions, may consequently be assumed as being equal to $10^{-5}$ kPa, whatever its real value may be.

Figure 5B:
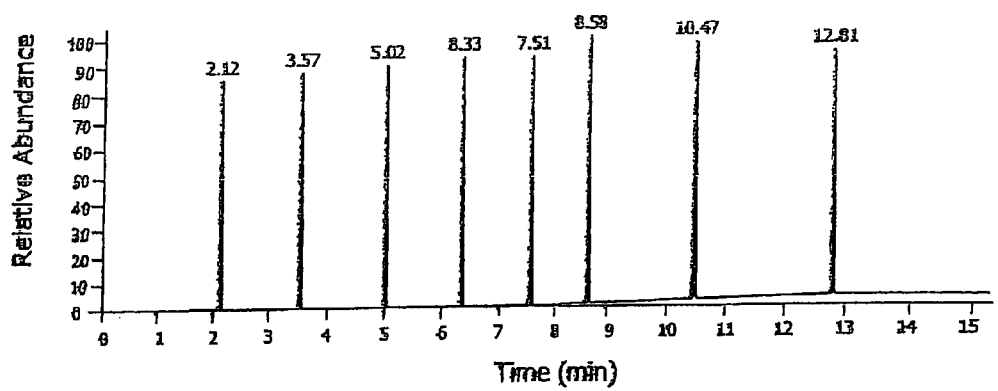

The same mixture was then analysed after the detector was replaced, setting the new value of $p_{i,new}$ and maintaining the temperature program constant. The results of the analysis are given in the chromatogram in FIG. 5b.

A numeric representation of the retention times in the two cases is provided in Table 2.

TABLE 2

| Component | Retention times (atmospheric-pressure detector (FID)) (min) | Retention times (detector under vacuum conditions (MS)) (min) | Difference (absolute value) (min) |
|---|---|---|---|
| C10 | 2.10 | 2.12 | 0.02 |
| C12 | 3.54 | 3.57 | 0.03 |
| C14 | 4.99 | 5.02 | 0.03 |
| C16 | 6.30 | 6.33 | 0.03 |
| C18 | 7.49 | 7.51 | 0.02 |
| C20 | 8.57 | 8.58 | 0.01 |
| C24 | 10.46 | 10.47 | 0.01 |
| C30 | 12.81 | 12.81 | 0.00 |

The invention claimed is:

1. A method for obtaining reproducibility of the retention times of the components of a mixture to be analysed in an apparatus for gaschromatographic analysis provided with a capillary column, when one or more of the following variations occurs: a variation in the length of the column, or alternatively replacement of the column with a column having identical real specifications with the exception of the length, and/or a variation in the output pressure from said column, given that the pneumatic resistance $KC_{old}=K(L_{old})$ of said column is known, the analytical expression of which is:

$$K(L_{old}) = \frac{256 \cdot L_{old}}{\pi \cdot d^4} \cdot \frac{\eta_0 \cdot P_{ref}}{T_{ref}^{1+\alpha}} \quad (9)$$

where:
- d is the diameter of the column;
- Pref, Tref are, respectively, the reference pressure and the reference temperature (referred to standard conditions);
- η0 is the viscosity of the carrier gas at the reference conditions;
- $L_{old}$ is the initial length of the column;
- α is the coefficient depending upon the type of carrier gas used;

and in which the temperature of said capillary column is maintained equal, instant by instant, starting from the introduction of the mixture into the apparatus, for each analysis of said mixture before and after one of said variations, characterized by the following steps:

measuring, prior to said variations, the pressure $p_{i,old}$ of the carrier gas at the input section of the column, and the pressure $p_{o,old}$ of the carrier gas at the output section of the column;

following upon said variations, measuring the new pneumatic resistance $KC_{new}$ $K(L_{new})$ of the column, the analytical expression of which is:

$$K(L_{new}) = \frac{256 \cdot L_{new}}{\pi \cdot d^4} \cdot \frac{\eta_0 \cdot P_{ref}}{T_{ref}^{1+\alpha}} \quad (5)$$

wherein:
- $L_{new}$ is the new length of the column;

selecting, after said variations, the new pressure $p_{o,new}$ at output from the column;

calculating a new input pressure $p_{i,new}$ or a new mass flow $F_{new}$ (referred to standard conditions) of the carrier gas, using the relation:

$$\lambda = \frac{j_{old}}{j_{new}} \cdot g \cdot \frac{p_{o,new}}{p_{o,old}} \quad (1)$$

where:

$$g = \frac{K(L_{new})}{K(L_{old})} = \frac{L_{new}}{L_{old}} \quad (2)$$

$$j_{new} = \frac{3}{2} \cdot \frac{\left(\frac{p_{i,new}}{p_{o,new}}\right)^2 - 1}{\left(\frac{p_{i,new}}{p_{o,new}}\right)^3 - 1} \quad (3)$$

$$j_{old} = \frac{3}{2} \cdot \frac{\left(\frac{p_{i,old}}{p_{o,old}}\right)^2 - 1}{\left(\frac{p_{i,old}}{p_{o,old}}\right)^3 - 1} \quad (4)$$

setting, after said variations, said new input pressure $p_{i,new}$ or said new mass flow $F_{new}$ of the carrier gas into said apparatus for gaschromatographic analysis in correlation to λ.

2. The method according to claim 1, in which said method the following steps:

storing the known quantities $K(L_{old})$, $K(L_{new})$, $p_{i,old}$, $p_{o,old}$, $p_{o,new}$ in electronic means for storage of said apparatus for gaschromatographic analysis;

storing the relation λ in said electronic storage means;

using λ for calculating and entering said quantity $F_{new}$ or $p_{i,new}$;

providing means for setting and control of the input pressure $p_{i,new}$ and/or of the flow rate $F_{new}$ in said apparatus for analysis.

3. The method according to claim 1, in which for calculation of said input pressure $p_{i,new}$ the following relation is used:

$$p_{i,new} = \sqrt{p_{o,new}^2 + \lambda \cdot g \cdot (p_{i,old}^2 - p_{o,old}^2)} \quad (6).$$

4. The method according to claim 1, in which for calculation of said mass flow $F_{new}$, the following steps are envisaged:

measuring the mass flow $F_{old}$, referred to standard conditions, of the carrier gas before said variations;

calculating said quantity $F_{new}$ using the relation:

$$F_{new} = F_{old} \cdot \lambda \quad (7).$$

5. The method according to claim 4, in which, if the temperature of said capillary column follows a trend which varies in time, the flow $F_{old}$ is measured or calculated instant by instant, and the flow $F_{new}$ is calculated instant by instant.

6. The method according to claim 1, in which for the calculation of said mass flow $F_{new}$, there are envisaged the steps of:

measuring, before said variations, the temperature $T_{col}$ of the capillary column;

calculating the mass flow $F_{old}$, referred to standard conditions, of the carrier gas before said variations, using the relation:

$$F_{old} = \frac{p_{i,old}^2 - p_{o,old}^2}{KC_{old} \cdot T_{col}^{1+\alpha}} \quad (8)$$

where:
- α is the coefficient depending upon the type of carrier gas used;
- $KC_{old}=K(L_{old})$ is the pneumatic resistance of the column according to relation (5) of claim 1;

calculating said quantity $F_{new}$, using the relation:

$$F_{new} = F_{old} \cdot \lambda \quad (6).$$

7. The method according to claim 1, in which said quantities $KC_{old}=K(L_{old})$ and $KC_{new}=K(L_{new})$ are measured by means of blank tests of said gaschromatographic apparatus.

* * * * *